(12) United States Patent
Rich

(10) Patent No.: US 8,303,894 B2
(45) Date of Patent: Nov. 6, 2012

(54) DETECTION AND FLUIDIC SYSTEM OF A FLOW CYTOMETER

(75) Inventor: Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 345 days.

(21) Appl. No.: 12/857,290

(22) Filed: Aug. 16, 2010

(65) Prior Publication Data

US 2010/0319469 A1 Dec. 23, 2010

Related U.S. Application Data

(63) Continuation-in-part of application No. 11/549,560, filed on Oct. 13, 2006, now Pat. No. 7,776,268, which is a continuation-in-part of application No. 11/370,714, filed on Mar. 8, 2006, now Pat. No. 8,017,402.

(60) Provisional application No. 60/727,144, filed on Oct. 13, 2005.

(51) Int. Cl.
*G01N 21/00* (2006.01)
*G01N 1/00* (2006.01)
*C12M 1/36* (2006.01)
*C12Q 3/00* (2006.01)
*B08B 7/00* (2006.01)
*G01N 35/08* (2006.01)

(52) U.S. Cl. ............ 422/67; 422/62; 422/68.1; 422/73; 422/82.05; 422/509; 73/863; 73/863.01; 73/863.02; 73/863.03; 73/864.34; 436/50; 436/52; 435/3; 435/286.1; 137/15.01; 137/565.01; 137/565.11

(58) Field of Classification Search .................. None
See application file for complete search history.

(56) References Cited

U.S. PATENT DOCUMENTS

| | | | |
|---|---|---|---|
| 3,347,273 A | 10/1967 | Russell |
| 3,061,128 A | 12/1968 | Hakim |
| 3,672,402 A | 6/1972 | Bloemer |
| 4,112,735 A | 8/1978 | McKnight |
| 4,138,879 A | 2/1979 | Liebermann |
| 4,371,786 A | 2/1983 | Kramer |
| 4,448,538 A | 5/1984 | Mantel |
| 4,559,454 A | 12/1985 | Kramer |
| 4,570,639 A | 2/1986 | Miodownik |
| 4,691,829 A | 9/1987 | Auer |
| 4,755,021 A | 7/1988 | Dyott |
| 4,790,653 A | 12/1988 | North, Jr. |
| 4,818,103 A | 4/1989 | Thomas et al. |

(Continued)

FOREIGN PATENT DOCUMENTS

EP 466490 A 1/1992

(Continued)

*Primary Examiner* — Neil N Turk
(74) *Attorney, Agent, or Firm* — Jeffrey Schox

(57) ABSTRACT

The fluidic system including a sheath pump that pumps sheath fluid from a sheath container into an interrogation zone, a waste pump that pumps waste fluid from the interrogation zone to a waste container, in which the flow rate of the sheath fluid is different from the flow rate of the waste fluid thereby drawing a sample fluid from a sample container into the interrogation zone, a detection system that provides a data set of input signals from the sample fluid, an analysis engine that recognizes aggregate particle events in the data set, and a controller that automatically adjusts the flow rate of the sample fluid into the interrogation zone based on the recognition of aggregate particle events, by controlling at least one of the flow rates of the sheath fluid and the waste fluid.

20 Claims, 2 Drawing Sheets

U.S. PATENT DOCUMENTS

| | | |
|---|---|---|
| 4,824,641 A | 4/1989 | Williams |
| 4,826,660 A | 5/1989 | Smith et al. |
| 4,844,610 A | 7/1989 | North, Jr. |
| 4,933,813 A | 6/1990 | Berger |
| 5,028,127 A | 7/1991 | Spitzberg |
| 5,040,890 A | 8/1991 | North, Jr. |
| 5,043,706 A | 8/1991 | Oliver |
| 5,083,862 A | 1/1992 | Rusnak |
| 5,138,868 A | 8/1992 | Long |
| 5,139,609 A | 8/1992 | Fields et al. |
| 5,150,037 A | 9/1992 | Kouzuki |
| 5,150,313 A | 9/1992 | van den Engh et al. |
| 5,155,543 A | 10/1992 | Hirako |
| 5,204,884 A | 4/1993 | Leary et al. |
| 5,224,058 A | 6/1993 | Mickaels et al. |
| 5,230,026 A | 7/1993 | Ohta et al. |
| 5,270,548 A | 12/1993 | Steinkamp |
| 5,301,685 A | 4/1994 | Guirguis |
| 5,308,990 A | 5/1994 | Takahashi et al. |
| 5,367,474 A | 11/1994 | Auer et al. |
| 5,374,395 A | 12/1994 | Robinson et al. |
| 5,395,588 A | 3/1995 | North, Jr. et al. |
| 5,403,552 A | 4/1995 | Pardikes |
| 5,466,946 A | 11/1995 | Kleinschmitt et al. |
| 5,469,375 A | 11/1995 | Kosaka |
| 5,539,386 A | 7/1996 | Elliott |
| 5,552,885 A | 9/1996 | Steen |
| 5,559,339 A | 9/1996 | Domanik et al. |
| 5,616,124 A | 4/1997 | Hague et al. |
| 5,684,480 A | 11/1997 | Jansson |
| 5,739,902 A | 4/1998 | Gjelsnes et al. |
| 5,797,430 A | 8/1998 | Becke et al. |
| 5,798,222 A | 8/1998 | Goix |
| 5,804,507 A | 9/1998 | Perlov et al. |
| 5,883,378 A | 3/1999 | Irish et al. |
| 5,920,388 A | 7/1999 | Sandberg et al. |
| 5,960,129 A | 9/1999 | Kleinschmitt |
| 5,981,180 A | 11/1999 | Chandler et al. |
| 6,016,376 A | 1/2000 | Ghaemi et al. |
| 6,039,078 A | 3/2000 | Tamari |
| 6,067,157 A | 5/2000 | Altendorf |
| 6,070,477 A | 6/2000 | Mark |
| 6,091,502 A | 7/2000 | Weigl et al. |
| 6,097,485 A | 8/2000 | Lievan |
| 6,108,463 A | 8/2000 | Herron et al. |
| 6,110,427 A | 8/2000 | Uffenheimer |
| 6,115,065 A | 9/2000 | Yadid-Pecht et al. |
| 6,139,800 A | 10/2000 | Chandler |
| 6,154,276 A | 11/2000 | Mariella, Jr. |
| 6,156,208 A | 12/2000 | Desjardins et al. |
| 6,181,319 B1 | 1/2001 | Fujita et al. |
| 6,183,697 B1 | 2/2001 | Tanaka et al. |
| 6,288,783 B1 | 9/2001 | Auad |
| 6,377,721 B1 | 4/2002 | Walt et al. |
| 6,382,228 B1 | 5/2002 | Cabuz et al. |
| 6,403,378 B1 | 6/2002 | Phi-Wilson et al. |
| 6,427,521 B2 | 8/2002 | Jakkula et al. |
| 6,431,950 B1 | 8/2002 | Mayes |
| 6,456,769 B1 | 9/2002 | Furusawa et al. |
| 6,469,787 B1 | 10/2002 | Meyer et al. |
| 6,473,171 B1 | 10/2002 | Buttry et al. |
| 6,519,355 B2 | 2/2003 | Nelson |
| 6,522,775 B2 | 2/2003 | Nelson |
| 6,568,271 B2 | 5/2003 | Shah et al. |
| 6,587,203 B2 | 7/2003 | Colon |
| 6,602,469 B1 | 8/2003 | Maus et al. |
| 6,636,623 B2 | 10/2003 | Nelson et al. |
| 6,675,835 B2 | 1/2004 | Gerner et al. |
| 6,694,799 B2 | 2/2004 | Small |
| 6,700,130 B2 | 3/2004 | Fritz |
| 6,710,871 B1 | 3/2004 | Goix |
| 6,718,415 B1 | 4/2004 | Chu |
| 6,778,910 B1 | 8/2004 | Vidal et al. |
| 6,809,804 B1 | 10/2004 | Yount et al. |
| 6,816,257 B2 | 11/2004 | Goix |
| 6,825,926 B2 | 11/2004 | Turner et al. |
| 6,852,284 B1 | 2/2005 | Holl et al. |
| 6,859,570 B2 | 2/2005 | Walt et al. |
| 6,869,569 B2 | 3/2005 | Kramer |
| 6,872,180 B2 | 3/2005 | Reinhardt et al. |
| 6,890,487 B1 | 5/2005 | Sklar et al. |
| 6,897,954 B2 | 5/2005 | Bishop et al. |
| 6,901,964 B2 | 6/2005 | Kippe et al. |
| 6,908,226 B2 | 6/2005 | Siddiqui et al. |
| 6,912,904 B2 | 7/2005 | Storm, Jr. et al. |
| 6,936,828 B2 | 8/2005 | Saccomanno |
| 6,941,005 B2 | 9/2005 | Lary et al. |
| 6,944,322 B2 | 9/2005 | Johnson et al. |
| 7,009,189 B2 | 3/2006 | Saccomanno |
| 7,012,689 B2 | 3/2006 | Sharpe |
| 7,019,834 B2 | 3/2006 | Sebok et al. |
| 7,024,316 B1 | 4/2006 | Ellison et al. |
| 7,061,595 B2 | 6/2006 | Cabuz et al. |
| 7,075,647 B2 | 7/2006 | Christodoulou |
| 7,105,355 B2 | 9/2006 | Kurabayashi et al. |
| 7,106,442 B2 | 9/2006 | Silcott et al. |
| 7,113,266 B1 | 9/2006 | Wells |
| 7,130,046 B2 | 10/2006 | Fritz et al. |
| 7,232,687 B2 | 6/2007 | Lary et al. |
| 7,262,838 B2 | 8/2007 | Fritz |
| 7,274,316 B2 | 9/2007 | Moore |
| 7,328,722 B2 | 2/2008 | Rich |
| 7,362,432 B2 | 4/2008 | Roth |
| 7,403,125 B2 | 7/2008 | Rich |
| 7,471,393 B2 | 12/2008 | Trainer |
| 7,520,300 B2 | 4/2009 | Rich |
| 7,628,956 B2 | 12/2009 | Jindo |
| 7,738,099 B2 | 6/2010 | Morrell et al. |
| 7,739,060 B2 | 6/2010 | Goebel |
| 7,776,268 B2 | 8/2010 | Rich |
| 7,780,916 B2 | 8/2010 | Bair et al. |
| 7,843,561 B2 | 11/2010 | Rich |
| 7,857,005 B2 | 12/2010 | Rich et al. |
| 7,981,661 B2 | 7/2011 | Rich |
| 7,996,188 B2 | 8/2011 | Olson et al. |
| 8,017,402 B2 | 9/2011 | Rich |
| 8,031,340 B2 | 10/2011 | Rich et al. |
| 2001/0014477 A1 | 8/2001 | Pelc et al. |
| 2001/0039053 A1 | 11/2001 | Liseo et al. |
| 2002/0028434 A1 | 3/2002 | Goix et al. |
| 2002/0049782 A1 | 4/2002 | Herzenberg et al. |
| 2002/0059959 A1 | 5/2002 | Qatu et al. |
| 2002/0080341 A1 | 6/2002 | Kosaka |
| 2002/0123154 A1 | 9/2002 | Burshteyn |
| 2002/0192113 A1 | 12/2002 | Uffenheimer et al. |
| 2003/0035168 A1 | 2/2003 | Qian et al. |
| 2003/0048539 A1 | 3/2003 | Oostman et al. |
| 2003/0054558 A1 | 3/2003 | Kurabayashi |
| 2003/0062314 A1 | 4/2003 | Davidson et al. |
| 2003/0072549 A1 | 4/2003 | Facer et al. |
| 2003/0078703 A1 | 4/2003 | Potts et al. |
| 2003/0129090 A1 | 7/2003 | Farrell |
| 2003/0134330 A1 | 7/2003 | Ravkin et al. |
| 2003/0148379 A1 | 8/2003 | Roitman et al. |
| 2003/0175157 A1 | 9/2003 | Micklash, II et al. |
| 2003/0202175 A1 | 10/2003 | Van den Engh et al. |
| 2003/0211009 A1 | 11/2003 | Buchanan |
| 2003/0223061 A1 | 12/2003 | Sebok |
| 2003/0235919 A1 | 12/2003 | Chandler |
| 2004/0031521 A1 | 2/2004 | Vrane et al. |
| 2004/0048362 A1 | 3/2004 | Trulson et al. |
| 2004/0112808 A1 | 6/2004 | Takagi et al. |
| 2004/0119974 A1 | 6/2004 | Bishop et al. |
| 2004/0123645 A1 | 7/2004 | Storm, Jr. et al. |
| 2004/0131322 A1 | 7/2004 | Ye et al. |
| 2004/0143423 A1 | 7/2004 | Parks et al. |
| 2004/0175837 A1 | 9/2004 | Bonne et al. |
| 2004/0201845 A1 | 10/2004 | Quist et al. |
| 2004/0246476 A1 | 12/2004 | Bevis et al. |
| 2005/0044110 A1 | 2/2005 | Herzenberg et al. |
| 2005/0047292 A1 | 3/2005 | Park et al. |
| 2005/0057749 A1 | 3/2005 | Dietz et al. |
| 2005/0069454 A1 | 3/2005 | Bell |
| 2005/0073686 A1 | 4/2005 | Roth et al. |
| 2005/0078299 A1 | 4/2005 | Fritz et al. |
| 2005/0105091 A1 | 5/2005 | Lieberman et al. |
| 2005/0162648 A1 | 7/2005 | Auer et al. |

| | | |
|---|---|---|
| 2005/0163663 A1 | 7/2005 | Martino et al. |
| 2005/0195605 A1 | 9/2005 | Saccomanno et al. |
| 2005/0195684 A1 | 9/2005 | Mayer |
| 2005/0252574 A1 | 11/2005 | Khan et al. |
| 2006/0002634 A1 | 1/2006 | Riley et al. |
| 2006/0015291 A1 | 1/2006 | Parks et al. |
| 2006/0023219 A1 | 2/2006 | Meyer et al. |
| 2006/0161057 A1 | 7/2006 | Weber et al. |
| 2006/0177937 A1 | 8/2006 | Kurabayashi et al. |
| 2006/0219873 A1 | 10/2006 | Martin et al. |
| 2006/0281143 A1 | 12/2006 | Liu et al. |
| 2006/0286549 A1 | 12/2006 | Sohn et al. |
| 2007/0003434 A1 | 1/2007 | Padmanabhan et al. |
| 2007/0041013 A1 | 2/2007 | Fritz et al. |
| 2007/0096039 A1 | 5/2007 | Kapoor et al. |
| 2007/0124089 A1 | 5/2007 | Jochum et al. |
| 2007/0127863 A1 | 6/2007 | Bair et al. |
| 2007/0144277 A1 | 6/2007 | Padmanabhan et al. |
| 2007/0212262 A1 | 9/2007 | Rich |
| 2007/0224684 A1 | 9/2007 | Olson et al. |
| 2007/0243106 A1 | 10/2007 | Rich |
| 2008/0055595 A1 | 3/2008 | Olson et al. |
| 2008/0064113 A1 | 3/2008 | Goix et al. |
| 2008/0092961 A1 | 4/2008 | Bair et al. |
| 2008/0152542 A1 | 6/2008 | Ball |
| 2008/0215297 A1 | 9/2008 | Goebel et al. |
| 2008/0228444 A1 | 9/2008 | Olson et al. |
| 2009/0104075 A1 | 4/2009 | Rich |
| 2009/0174881 A1 | 7/2009 | Rich |
| 2009/0201501 A1 | 8/2009 | Bair et al. |
| 2009/0202130 A1 | 8/2009 | George et al. |
| 2009/0216478 A1 | 8/2009 | Estevez-Labori |
| 2009/0260701 A1 | 10/2009 | Rich |
| 2009/0293910 A1 | 12/2009 | Ball et al. |
| 2010/0012853 A1 | 1/2010 | Parks |
| 2010/0032584 A1 | 2/2010 | Dayong et al. |
| 2010/0118298 A1 | 5/2010 | Bair et al. |
| 2010/0302536 A1 | 12/2010 | Ball et al. |
| 2010/0319469 A1 | 12/2010 | Rich |
| 2010/0319786 A1 | 12/2010 | Bair |
| 2011/0008816 A1 | 1/2011 | Ball et al. |
| 2011/0058163 A1 | 3/2011 | Rich |
| 2011/0061471 A1 | 3/2011 | Rich et al. |
| 2011/0306031 A1 | 12/2011 | Rich |

FOREIGN PATENT DOCUMENTS

| | | |
|---|---|---|
| EP | 1391611 A | 2/2004 |
| EP | 1396736 A | 3/2004 |
| EP | 1521076 | 9/2004 |
| JP | 356169978 A | 12/1981 |
| JP | Sho5913689 | 3/1984 |
| JP | Sho6353901 | 4/1988 |
| JP | 04086546 H | 3/1992 |
| JP | 6194299 A | 7/1994 |
| JP | 06221988 H | 12/1994 |
| JP | 7260084 A | 10/1995 |
| JP | 08201267 H | 8/1996 |
| JP | 09288053 H | 11/1997 |
| JP | 10227737 A | 8/1998 |
| JP | 2001050887 A | 2/2001 |
| JP | 2001170062 A | 6/2001 |
| JP | 2003262201 A | 9/2003 |
| JP | 200477484 | 3/2004 |
| WO | 9956052 | 11/1999 |
| WO | 0194914 | 12/2001 |
| WO | WO 2005/068971 | 1/2005 |
| WO | WO 2005/017499 | 2/2005 |
| WO | WO 2005/091893 | 2/2005 |
| WO | 2005073694 A | 8/2005 |
| WO | WO 2006/055722 | 5/2006 |
| WO | WO 2007/103969 | 3/2007 |
| WO | 2007067577 A | 6/2007 |
| WO | 2007100723 A | 9/2007 |
| WO | 2007136749 A | 11/2007 |
| WO | WO 2008/058217 | 5/2008 |
| WO | 2010101623 A | 9/2010 |

DETECTION AND FLUIDIC SYSTEM OF A FLOW CYTOMETER

CROSS-REFERENCE TO RELATED APPLICATIONS

This application is a continuation-in-part of prior application Ser. No. 11/549,560 filed 13 Oct. 2006, which is a continuation-in-part of prior application Ser. No. 11/370,714 filed 8 Mar. 2006 and claims the benefit of U.S. Provisional Application No. 60/727,144 filed 13 Oct. 2005, all of which are incorporated in their entirety by this reference.

This application is also related to U.S. Pat. No. 7,739,060 filed 21 Dec. 2007 and to U.S. patent application Ser. No. 12/770,341 filed 29 Apr. 2010, which are both incorporated in their entirety by this reference.

TECHNICAL FIELD

This invention relates generally to the flow cytometer field, and more specifically to an improved fluidic system in the flow cytometer field.

BACKGROUND

In typical flow cytometry systems, the fluidics system functions to draw sample particles into a sample stream and transport the sample stream through an interrogation zone. The fluidics system typically uses a pressurized sheath stream to hydrodynamically focus the sample stream, which is known as the core stream, within the center of the sheath stream. The process of hydrodynamic focusing (also known as coaxial flow) results in laminar flow under preferred conditions and enables the optical system of the flow cytometer to illuminate, and thus analyze, the sample particles with uniformity and repeatability. Ideally, the particles within the core stream are positioned in the center of the interrogation zone. For many applications, particles are ideally arranged in a "single file" line within the core stream, although for other applications the ideal core stream may have a different arrangement of particles. For instance, one common problem in flow cytometry is the necessity for coincident detection of multiple particles known generally as "aggregate particles" that are closely spaced or joined in the sample. Depending on the experiment, closely spaced aggregate particles can either be undesirable (compromising data such as by causing ambiguity regarding which particle an input signal is for) or desirable (such as cells in the process of cell division/mitosis). To accomplish a particular particle arrangement across multiple sample particle sizes, the core stream is typically adjusted in an open loop manner by multiple controls that alter (1) the pressure of the sample line, (2) the pressure of the sheath line, and (3) the sample-to-sheath pressure differential. Most commonly, at least two of the three settings will need to be adjusted in the course of setting the core stream size.

Adjusting the multitude of controls used to set the core stream, including the sample flow rate (i.e. sample line pressure), sheath flow rate (i.e. sheath line pressure), and sample-to-sheath pressure differential often requires multiple iterations of adjustments. Setting the multiple control flow cytometer core stream controls can be challenging to, and time consuming for, the experienced user, and can lead to inaccurate data (i.e. event) collection and suboptimal core stream formation in the hands of an inexperienced user. Furthermore, a substantial amount of sample must be consumed in order to set the pressure settings, which is a further disadvantage of the present system particularly when the sample to be analyzed is available in a very limited quantity.

Thus, there is a need in the flow cytometer field to create a new, improved, and useful fluidic system that avoids or minimizes these disadvantages. This invention provides such a new, improved, and useful detection and fluidic system for a flow cytometer.

DESCRIPTION OF THE PREFERRED EMBODIMENT

The following description of the preferred embodiment of the invention is not intended to limit the invention to this preferred embodiment, but rather to enable any person skilled in the art of flow cytometers to make and use this invention.

Figure 1:
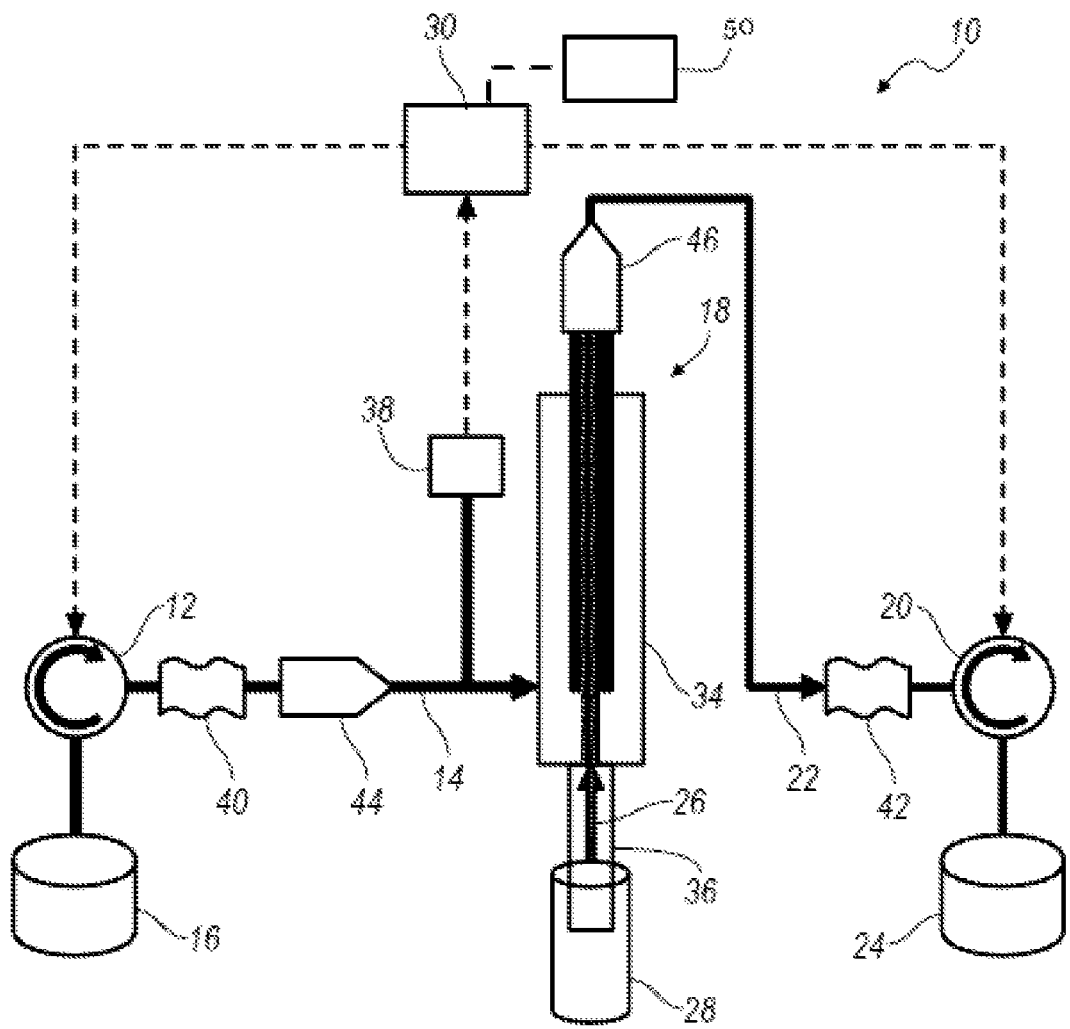
FIG. 1 is a schematic representation of the fluidic system of the preferred embodiment of the invention.
Figure 2:
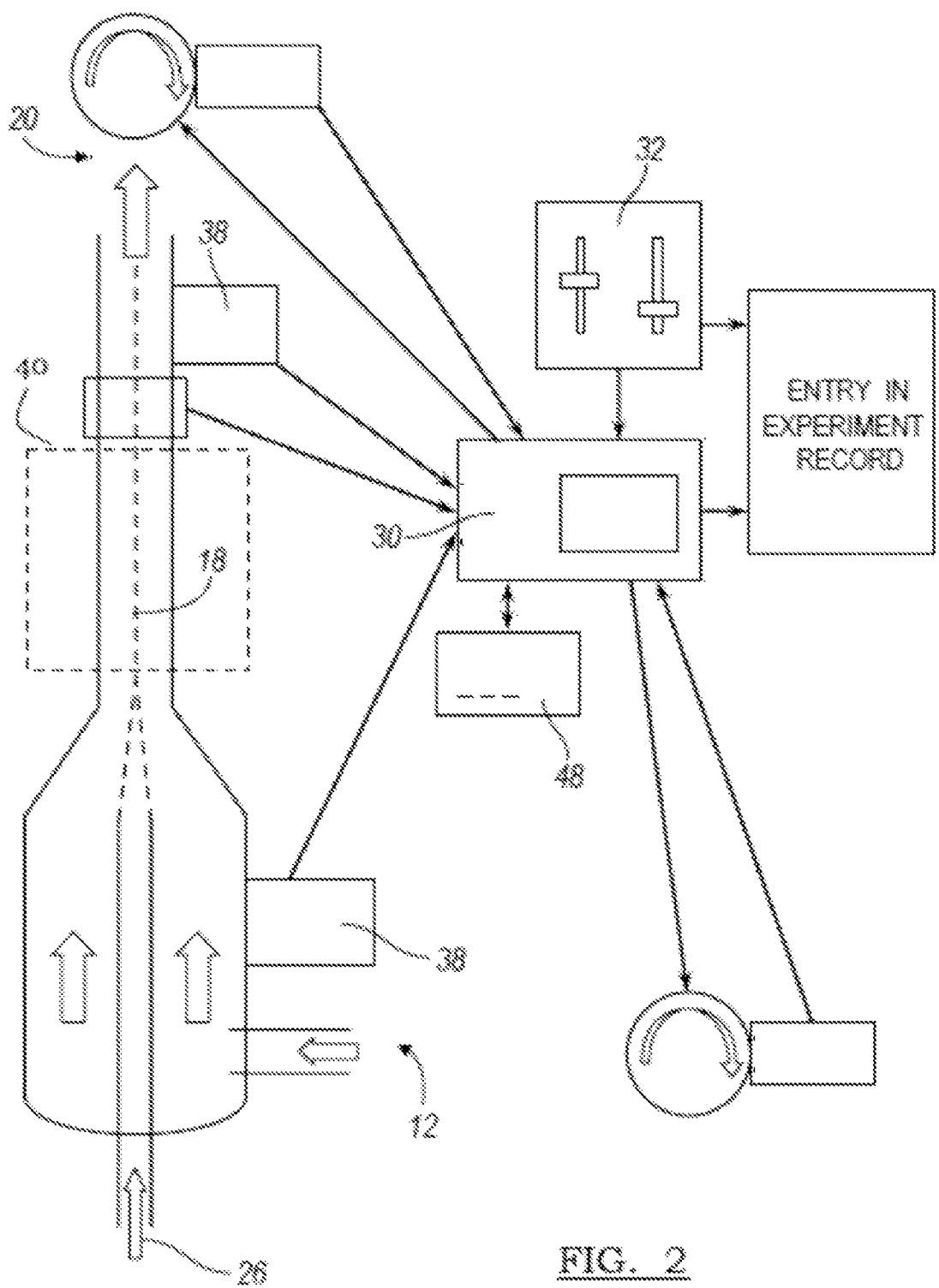
FIG. 2 is a schematic representation of the user interface of the preferred embodiment of the invention

As shown in FIGS. 1 and 2, the fluidic system 10 of the preferred embodiment includes a sheath pump 12 to pump sheath fluid 14 from a sheath container 16 into an interrogation zone 18 and a waste pump 20 to pump the sheath fluid 14 and a sample fluid 26 as waste fluid 22 from the interrogation zone 18 into a waste container 24. The sheath pump 12 and/or the waste pump 20 draw sample fluid 26 from a sample container 28 into the interrogation zone 18. The fluidic system 10 also includes a detection system 40 coupled to the interrogation zone 18 that provides a data set of input signals from the sample fluid, an analysis engine 50 that recognizes aggregate particle events in the data set, and a controller 30 to adjust the flow rate of the sample fluid 26 from the sample container 28 into the interrogation zone 18. The controller 30 preferably automatically adjusts the flow rate of the sample fluid 26 based on the recognition of aggregate particle events by controlling at least one of the flow rates of the sheath fluid 14 and the waste fluid 22. The controller may arrange particles in a "single file" line within the core stream, although for other applications the ideal core stream may have a different arrangement of particles. For instance, depending on the experiment, closely spaced aggregate particles can either be undesirable (compromising data such as by causing ambiguity regarding which particle an input signal is for) and are in one way prevented by having a relatively narrow core stream, or desirable (such as cells in the process of cell division/mitosis) and are in one way facilitated by having a relatively wider core stream. The fluidic system 10 may also include a user interface 32 to receive an input from a user. The interrogation zone 18 functions to provide a location for the fluidic system 10 and an optical system of the flow cytometer to cooperatively facilitate the analysis of the sample fluid 26. The interrogation zone 18 is preferably enclosed within a removable flow cell 34, but may alternatively be defined by any suitable system or device. The fluidic system 10 is preferably incorporated into a flow cytometer, but may be alternatively incorporated into any suitable system that pumps a first fluid from a first container into an interrogation zone 18, draws a second fluid from a second container into the interrogation zone 18, and pumps the combined fluids from the interrogation zone 18 into a third container.

As shown in FIG. 1, the sheath pump 12 of the preferred embodiment functions to pump sheath fluid 14 from a sheath container 16 into an interrogation zone 18. The sheath fluid 14 functions to hydrodynamically focus the sample fluid 26. The process of hydrodynamic focusing results in laminar flow of the sample fluid 26 within the flow cell 34 and enables the optical system to illuminate, and thus analyze, the particles within the sample fluid 26 with uniformity and repeatability. Preferably, the sheath fluid 14 is buffered saline or de-ionized water, but the sheath fluid 14 may alternatively be any suitable fluid to hydrodynamically focus the sample fluid 26. The sheath container 16 functions to contain the sheath fluid 14. The sheath container 16 is preferably a vented tank with a volume of approximately 1 L, but the sheath tank may alternatively be any suitable container to contain the sheath fluid 14. Preferably, the sheath pump 12 is a positive displacement pump. More preferably, the sheath pump 12 is a peristaltic pump with a flexible tube and one or more cams that pump the sheath fluid 14 through the flexible tube. The sheath pump 12 preferably has a known flow rate to pump speed ratio, such that control of the speed of the sheath pump 12 corresponds to a control of the flow rate of the sheath fluid 14. With this pump type, the fluidic system 10 is relatively easy to assemble, light to haul, quick to control, and easy to clean. Alternatively, the sheath pump 12 may be any suitable pump that pumps sheath fluid 14 from a sheath container 16 into an interrogation zone 18.

The waste pump 20 of the preferred embodiment functions to pump the waste fluid 22 from the interrogation zone 18 into a waste container 24. Preferably, the waste fluid 22 includes the sheath fluid 14 and the sample fluid 26. Alternatively, the waste fluid 22 may include any fluid that exits the interrogation zone 18. The waste container 24 is preferably a vented tank with a volume of approximately 1 L, but the waste tank may alternatively be any suitable container to contain the waste fluid 22. Like the sheath pump 12, the waste pump 20 is preferably a positive displacement pump and more preferably a peristaltic pump with a flexible tube and one or more cams that pump the waste fluid 22 through the flexible tube. The waste pump 20 preferably has a known flow rate to pump speed ratio, such that control of the speed of the waste pump 20 corresponds to a control of the flow rate of the waste fluid 22. With this pump type, the fluidic system 10 is relatively easy to assemble, light to haul, quick to control, and easy to clean. Alternatively, the waste pump 20 may be any suitable pump that pumps waste fluid 22 from a waste container 24 into an interrogation zone 18.

The sheath pump 12 and the waste pump 20 of the preferred embodiment cooperate to draw the sample fluid 26 from the sample container 28 and through a drawtube 36. The sample fluid 26 contains particles to be analyzed by the flow cytometer. The sample fluid 26 is preferably blood, but the sample fluid 26 may alternatively be any suitable fluid to be analyzed by the flow cytometer. The sample container 28, which functions to contain the sample fluid 26, is preferably an open beaker with a volume of approximately 5 mL, but may alternatively be any suitable container to contain the sample fluid 26. The drawtube 36, functions to convey the sample fluid 26 from the sample container 28 into the interrogation zone 18, is a conventional drawtube, but may alternatively be any suitable device to convey the sample fluid 26.

The sheath pump 12 and the waste pump 20 preferably cooperate to draw the sample fluid 26 from the sample container 28 into the interrogation zone 18 through the use of a pressure differential (e.g., the sheath pump 12 "pushes" the sheath fluid 14 and the waste pump 20 "pulls" the sheath fluid 14 and the sample fluid 26). In order to allow a variable flow rate of the sample fluid 26, the fluidic system 10 preferably allows for a variable flow rate of the sheath fluid 14 and/or the waste fluid 22. In a first variation, the sheath pump 12 and the waste pump 20 are driven by a single motor, but with a variable drive ratio device (e.g., transmission), such that the sheath pump 12 and the waste pump 20 may be operated at different pump speeds and, therefore, allow for a variable flow rate of the sheath fluid 14 and/or the waste fluid 22. In a second variation, the sheath pump 12 and the waste pump 20 are driven by a single motor, but the fluidic system 10 includes at least one by-pass valve located near the sheath pump 12 and/or the waste pump 20. The by-pass valve diverts a variable amount of the fluid flow and, therefore, allows for a variable flow rate of the sheath fluid 14 and/or waste fluid 22. In a third variation, the sheath pump 12 and the waste pump 20 are driven by a single motor, but the fluidic system 10 includes at least one restrictive valve located near the sheath pump 12 and/or the waste pump 20. The restrictive valve alters the fluid flow and, therefore, allows for a variable flow rate of the sheath fluid 14 and/or waste fluid 22. In a fourth variation, the sheath pump 12 and the waste pump 20 are driven by separate motors with separate controls and, therefore, allows for a variable flow rate of the sheath fluid 14 and/or waste fluid 22. The fluidic system 10 may, however, include other suitable variations that draw the sample fluid 26 from the sample container 28 into the interrogation zone 18 through the use of a pressure differential.

The detection system 40 of the preferred embodiment functions to provide a data set of input signals from the interrogation zone 18 for the sample fluid. The detection system 40 preferably receives photonic inputs from the interrogation zone 18 and produces analog and/or digital signals based on these photonic inputs. The detection system 40 is preferably operable over a wide dynamic range, and as used herein, the term "wide dynamic range" is preferably defined as greater than or equal to 100 dB. The data set provided by the detection system 40 preferably allows for the recognition of aggregate particle events, as well as non-aggregate particle events.

The analysis engine 50 functions to recognize aggregate particle events in the data set, and in some embodiments, further functions to recognize non-aggregate particle events in the data set. The analysis engine 50, which preferably interfaces with the detection system 40, preferably applies gain and scaling factors to the acquired data, independent of the acquisition step. The analysis engine 50 preferably also includes an algorithm that is able to recognize aggregate particle events. The algorithm preferably recognizes the characteristic "peak-trough-peak" waveform produced by aggregate particle events and may annotate the events accordingly while simultaneously preserving the raw, unmodified data. The algorithm may additionally or alternatively recognize other characteristic aspects, such as a unique width versus height or area for the waveform. Each event is preferably labeled as either an "aggregate particle event" or "doublet" or a "non-aggregate particle event", but may alternatively be labeled in any other suitable fashion such as labeling the number of aggregate particles, labeling a descriptor of the separation between the two particles (such as 20% conjoined or "loosely connected") based on the peak versus trough ratios, labeling if the aggregate particle is a contaminant, or labeling if the aggregate particle is a cell undergoing cell division or mitosis.

The detection system 40 and analysis engine 50 are preferably similar to those described in U.S. Pat. No. 7,739,060 entitled "Detection system and user interface for a flow cytometer system", which is hereby incorporated in its entirety by this reference. However, the detection system 40 and/or analysis engine 50 may alternatively be any suitable detection system or analysis engine.

The controller 30 of the preferred embodiment functions to adjust the flow rate of the sample fluid 26 from the sample container 28 into the interrogation zone 18. Preferably, the controller 30 adjusts the flow rate of the sample fluid 26 by adjusting the variable flow rate of the sheath fluid 14 and/or the waste fluid 22. More preferably, the controller 30 adjusts the flow rate of the sample fluid 26 by allowing an adjustable flow rate of the sheath fluid 14 from the sheath container 16 to the interrogation zone 18, while maintaining a consistent flow rate of the waste fluid 22 from the interrogation zone 18 into the waste container 24. The advantage of this arrangement is a finer control of the flow rate of the sample fluid 26. Alternatively, the controller 30 may adjust the flow rate of waste fluid 22 while maintaining the flow rate of the sheath fluid 14, or may simultaneously adjust the flow rates of the sheath fluid 14 and the waste fluid 22. Furthermore, the controller 30 may employ one technique (such as allowing an adjustable flow rate of the sheath fluid 14, while maintaining a consistent flow rate of the waste fluid 22) in most situations, and may employ another technique (such as simultaneously adjusting the flow rates of the sheath fluid 14 and the waste fluid 22) in other situations to quickly response to a user input. The controller 30 is preferably a proportional-integral-derivative (PID) controller, but may alternatively be a proportional-integral (PI) controller, a proportional-derivative (PD) controller, a proportional (P) controller, or any other suitable controller.

As shown in FIG. 2, the fluidic system 10 of the preferred embodiment also includes a user interface 32 that facilitates the receipt of an input from a user that controls the controller 30 (also called a core stream controller). The user interface 32 is connected to the controller 30 and functions to allow adjustment of the flow rate of the sample fluid 26 from the sample container 28 into the interrogation zone 18. The input from the user is preferably a single adjustment, or a more intuitive input from the user, and preferably is at least one of following three parameters: a desired core stream diameter, a core stream fluid type, and an estimated sample particle size. Preferably, the user interface 32 is internally based on flow rates of the sheath fluid and/or the waste fluid, but externally based on one of above three parameters. In contrast to conventional flow cytometry systems, the user sets the flow rate of the sample fluid based on intuitive controls, rather than the sample stream flow rate/pressure, sheath stream flow rate/pressure, and/or sample-to-sheath pressure differential, in order to achieve near-optimal flow.

In a first variation, the controller 30 preferably accesses a lookup table to correlate the input from the user to the flow rate of the sample fluid. The lookup table preferably includes data based on previous sample runs of the flow cytometer, based on sample runs by users of different—yet comparable—flow cytometers (e.g. researchers studying at a remote R&D facility), and/or based on empirical data conducted and developed by the manufacturer or developer of the flow cytometer system. The stored information preferably includes the type of the core stream fluid, the identification of the sample particle, and flow rate of the sample fluid, but may alternatively include any suitable information. The controller 30 may also be further adapted to access the lookup table via a computer network.

In a second variation, the controller 30 preferably includes a storage device 48 with accessible memory. The user interface 32 and accessible memory permit the user to access stored information about similar sample runs and the system configuration and settings that were utilized during those runs. The stored information preferably includes the date of the sample run, the type of the core stream fluid, the identification of the sample particle, and flow rate of the sample fluid, identification of the user, the date of the sample run, exemplary data, and comments from the user, but may alternatively include any suitable information. This stored information can be accessed by the user and retrieved by the controller 30 and flow cytometry system. The user can then, by simply interfacing with the controller 30, automatically set up the pressures and/or flow rates of the sample, sheath, and/or waste streams utilizing those previous sample run settings. Furthermore, once the user has completed a sample run, they can save the controller settings and use the saved information for future sample runs. In a variation of this embodiment, the accessible memory in the flow cytometry system is capable of retrieving remotely saved information about sample runs on similar flow cytometer systems and sample types via a computer network.

Examples of sample run information suitable for later use include: user identification and contact information; date of sample run; identification of the flow cytometer system; identification of the type of flow cytometry analyses conducted (e.g. sorting based on a given wavelength, sample particle counting); type of sample analyzed (e.g. mammalian fibroblast cells, FITC-labeled leukocytes, BODIPY-conjugated proteins, etc.); type of sheath fluid used (e.g. phosphate buffered saline, air); exemplary data from the run (e.g. screen shots, text, or graph files); notes intended for future reference (e.g. problems, suggestions); and, of course, pressure and/or flow rates associated with the sample, sheath, and/or waste streams. Previous sample run information can be stored and accessed by any suitable means from any suitable location or device. Examples of how run information could be saved and accessed include: file name, date of sample run, or type of sample to be analyzed. Sample run data may be stored on a computer component within the flow cytometer system, on a computer network, or in any other suitable location or system.

In another variation, the flow cytometry system of the preferred embodiment includes a core stream detector connected to, and in communication with, the controller 30 to achieve an optimum core stream. The core stream detector functions to identify basic core stream characteristics and transmits the information to the controller 30. Based on this information, the controller 30 dynamically alters the pressures and/or flow rates of the sample, sheath, and/or waste streams in order to approach an optimal core stream. Thus, the core stream detector and the information act as a feedback loop. The core stream detector preferably detects any suitable core stream characteristics. Examples of characteristics include the actual core stream diameter, time elapsed between the passage of sample particles through the interrogation zone, and flow rate of sample particles through the interrogation zone. The core stream detector is preferably located nearby the interrogation zone 18, but may be alternatively located in any suitable location and physically combined with other components of the flow cytometer system. For example, the core stream detector may alternatively be connected to a processor and may receive and transmit information about the acquired data, such as the coefficient variation of the acquired data. In addition, the controller 30 may receive information about other characteristics affecting the core stream from the optical components of the flow cytometry system, such as the time of flight of the sample particles and the number of particles per second that pass through the interrogation zone. The flow cytometer system and/or the controller 30 may dynamically change the parameters of the sample, sheath, and/or waste lines during the analysis of a sample to maintain a particular sample particle velocity, sample fluid flow rate, coefficient variation of the acquired data, or any other suitable parameter. This dynamic change could be predetermined (e.g., to incorporate different parameter settings for different trials), or could be based on an appropriate feedback.

In yet another variation, the flow cytometry system of the preferred embodiment includes a core stream detector connected to, and in communication with, a processor. Like the above variation, this core stream detector functions to identify basic core stream characteristics and transmit this information. Unlike the above variation, however, this information is used to electronically compensate and adjust the acquired data to achieve consistent data.

In another embodiment, the controller 30 preferably automatically adjusts the flow rate of the sample fluid 26 into the interrogation zone 18 based on the recognition of aggregate particle events by the analysis engine 50. In particular, the controller 30 preferably automatically adjusts (i.e., in real time or near real time, without explicit user input) the core stream diameter of the sample fluid 26 in response to the recognition of an aggregate particle event by the analysis engine. As used herein, the term "automatic" is preferably defined as capable of acting or operating in a manner essentially independent of user input. Adjustments may additionally and/or alternatively be made in response to recognition of a non-aggregate particle event. Such adjustments may be progressively incremental (progressively more drastic) after a particle event recognition and/or only up to a certain flow rate or core stream diameter. The controller may be one or more of several variations.

In a first variation, the controller decreases the core stream diameter when the analysis engine recognizes an aggregate particle event in the data set. For example, when the analysis engine recognizes an aggregate particle event in which two or more particles in the sample fluid closely spaced to each other have passed through the interrogation zone, the controller preferably automatically reduces the core stream diameter such that the sample particles in the core stream flow in single file at least while passing through the interrogation zone. The reduced core stream diameter may be approximately a known diameter of a sample particle (if the sample particle type is known), or may be any reduced core stream diameter. In some instances, the controller may progressively decrease the core stream diameter until the diameter is of a suitable size (e.g., the controller decreases the core stream diameter incrementally each time the analysis engine recognizes an aggregate particle event in the data set). As a result, the controller preferably adjusts sample fluid flow and core stream diameter to reduce the occurrence of aggregate particles in the core stream and consequent aggregate particle events in the data.

In a second variation, the controller increases the core stream diameter when the analysis engine recognizes a non-aggregate particle event in the data set. Recognition of a non-aggregate particle event may indicate that the core stream diameter can be increased, thereby increasing sample fluid flow rate, allowing faster passage of sample fluid through the interrogation zone, and increasing efficiency of analysis of a particular sample.

In a third variation, the controller increases the core stream diameter when the analysis engine recognizes an aggregate particle event in the data set. For example, this variation may be advantageous in applications in which aggregate particles are expected and/or desired to pass through the interrogation site. By increasing the sample fluid rate and the core stream diameter, the controller may allow passage of aggregate particles while increasing speed, thereby optimizing overall speed of a sample run.

In a fourth variation, the controller decreases the core stream diameter when the analysis engine recognizes a non-aggregate particle event in the data set, which may be useful in some applications.

In each of these variations, the controller preferably adjusts the sample flow rate and/or core stream diameter based on an adjustment algorithm. For example, the controller may automatically adjust the flow rate of the sample fluid and/or the core stream diameter after the analysis engine has recognized a predetermined number of aggregate particle events (e.g., one, two, or five) in the data set. As another example, the controller may automatically adjust the flow rate of the sample fluid and/or core stream diameter after the analysis engine has recognized a certain threshold percentage of aggregate particles, such as a predetermined ratio of aggregate particle events to non-aggregate particle events in the data set. The controller adjustment algorithm may additionally and/or alternatively include criteria such as a pattern of continuously recognized particle events, or any suitable criteria.

Additional embodiments of the controller include every combination of the variations. Furthermore, any combination of the variations may be used to continuously and/or repeatedly adjust the sample fluid flow rate and core stream diameter. For example, in a combination of the first and second variations, overall efficiency of sample analysis may be increased or optimized without compromising data as a result of aggregate particles in the sample, by (1) decreasing sample flow rate when the analysis engine recognizes aggregate particle events and (2) increasing sample flow rate when the analysis engine recognizes non-aggregate particle events, such that increasing flow rate when aggregate particle events are presumed to be less likely to affect collected data.

As shown in FIG. 1, the fluidic system 10 of the preferred embodiment also includes a pressure sensor 38 that functions to measure a pressure of the sheath fluid 14 as close as possible to the inlet for the sample fluid 26. This measured pressure is an adequate estimate for the pressure of the sample fluid 26. The pressure sensor 38 preferably measures a pressure differential between the top of the drawtube 36 near the flow cell 34 and the bottom of the drawtube 36 near the sample container 28, but may alternatively measure a pressure differential between the drawtube 36 and atmosphere. The controller 30 is preferably connected to the pressure sensor 38 and adjusts the flow rate of the sample fluid 26 based on the measured pressure. The controller 30 may alternatively or additionally be connected to other suitable devices to assist in the control of the flow rate of the sample fluid 26. In a first variation, the fluidic system 10 may include a flow meter that functions to measure the flow rate of the sample fluid 26 from the sample container 28 into the interrogation zone 18. In a second variation, the fluidic system 10 may include an input device that functions to receive information related to a fluidic resistance of a drawtube 36 that transports the sample fluid 26 from the sample container 28 into the interrogation zone 18. The input device is preferably an optical device (e.g., a bar code scanner) or an electromagnetic device (e.g., a RFID receiver) that functions to automatically scan and read a code on the drawtube 36. The code is preferably cross-referenced with empirically derived information regarding the fluidic resistance of the drawtube 36. The input device may alternatively be a user-interface device that accepts a code or value related to the fluidic resistance of the drawtube 36. In a third variation, the fluidic system 10 may be substantially self-calibrating according to the following steps: the user places a drawtube 36 of the flow cell 34 into a known fluid (such as buffered saline), the user pumps waste fluid 22 from the interrogation zone 18 into a waste container 24 while maintaining a negligible flow rate of the sheath fluid 14 thereby drawing the known fluid through the drawtube 36 and into the interrogation zone 18, and the fluidic system 10 (through measurement of the flow rate of the waste fluid 22 or any other suitable parameter) estimates the resistance of the drawtube 36. With this estimated resistance of the drawtube 36 for the flow cell 34 combined with the measured pressure of the sheath fluid 14, the controller 30 adjusts the flow rate of the sample fluid 26 with greater accuracy and control.

The fluidic system 10 of the preferred embodiment also includes a first fluidic capacitor 40 located between the sheath container 16 and the interrogation zone 18 and a second fluidic capacitor 42 located between the interrogation zone 18 and the waste container 24. The fluidic capacitors 40 and 42 function to attenuate pulsations within the fluidic system 10. More specifically, the first fluidic capacitor 40 functions to temporarily expand/contract to thereby accumulate/release the sheath fluid 14 and attenuate pulsations within the sheath fluid 14. Similarly, the second fluidic capacitor 42 functions to temporarily expand/contract to thereby accumulate/release the waste fluid 22 and attenuate pulsations within the waste fluid 22. The fluidic capacitors 40 and 42 are selected from the group consisting of bellows-type with a diaphragm, bellows-type without a diaphragm, captive ball-type, and flexible tube-type. The fluidic capacitors 40 and 42 are preferably similar to the fluidic attenuators described in U.S. patent application Ser. No. 11/297,667 entitled "Pulsation Attenuator For A Fluidic System" and filed 7 Dec. 2005, which is hereby incorporated in its entirety by this reference. The fluidic capacitors 40 and 42 may, however, be any suitable device to attenuate pulsations within the fluidic system 10.

The fluidic system 10 of the preferred embodiment also includes a valve 44 located between the first fluidic capacitor and the interrogation zone 18, and a valve 46 located between the interrogation zone 18 and the second fluidic capacitor. The valves 44 and 46 function to facilitate the control of the sheath fluid 14 and the waste fluid 22. The valves 44 and 46 are preferably check-valves, but may alternatively be any suitable valve to facilitate the control of the sheath fluid 14 and the waste fluid 22.

The detection and fluidic system of a preferred embodiment is operated with the following steps: (1) simultaneously pumping sheath fluid 14 from the sheath container 16 into the interrogation zone 18 of the flow cytometer and pumping waste fluid 22 from the interrogation zone 18 into a waste container 24, in which the flow rate of the sheath fluid is different from the flow rate of the waste fluid, thereby drawing the sample fluid 26 from the sample container 28 into the interrogation zone; (2) collecting a data set of input signals from the sample fluid 26; (3) recognizing aggregate particle events in the data set with use of an algorithm; and (4) automatically adjusting the flow rate of the sample fluid 26 into the interrogation zone 18 based on the recognition of aggregate particle events in the data set, wherein adjusting the flow rate of the sample fluid 26 includes controlling at least one of the flow rates of the sheath fluid 14 and the waste fluid 22.

As a person skilled in the art of flow cytometers will recognize from the previous detailed description and from the figures and claims, modifications and changes can be made to the preferred embodiment of the invention without departing from the scope of this invention defined in the following claims.

I claim:

1. A fluidic system for drawing sample fluid from a sample container, into an interrogation zone of a flow cytometer, comprising:

a sheath pump that pumps sheath fluid at a sheath flow rate from a sheath container through a flow cell into the interrogation zone of the flow cytometer, wherein the flow cell is fluidically coupled to the sample container;

a waste pump that pumps waste fluid at a waste flow rate from the interrogation zone into a waste container;

wherein the sheath flow rate is different from the waste flow rate, thereby creating a pressure differential, and wherein the pressure differential draws the sample fluid from the sample container, through the flow cell with the sheath fluid into the interrogation zone at a sample flow rate;

a detection system coupled to the interrogation zone that provides a data set of input signals from the sample fluid;

an analysis engine that recognizes aggregate particle events in the data set; and a controller that automatically adjusts the sample flow rate based on the recognition of aggregate particle events by controlling at least one of the sheath flow rate and the waste flow rate to adjust the pressure differential.

2. The fluidic system of claim 1, wherein the controller automatically adjusts a core stream diameter of the sample fluid in response to the recognition of an aggregate particle event.

3. The fluidic system of claim 2, wherein the controller decreases the core stream diameter when the analysis engine recognizes an aggregate particle event in the data set.

4. The fluidic system of claim 3, wherein the controller decreases the core stream diameter to approximately the diameter of a single sample particle in response to the recognition of an aggregate particle event, such that sample particles in the sample fluid flow in single file into the interrogation zone.

5. The fluidic system of claim 3, wherein the analysis engine further recognizes non-aggregate particles events, wherein the controller increases the core stream diameter when the analysis engine recognizes a non-aggregate particle event in the data set.

6. The fluidic system of claim 2, wherein the controller increases the core stream diameter when the analysis engine recognizes an aggregate particle event in the data set.

7. The fluidic system of claim 1, wherein the controller automatically adjusts the sample flow rate after a predetermined number of aggregate particle events is recognized.

8. The fluidic system of claim 1, wherein the analysis engine further recognizes non-aggregate particle events, wherein the controller automatically adjusts the sample flow rate after a predetermined ratio of aggregate particle events to non-aggregate particle events is recognized.

9. The fluidic system of claim 1, wherein the analysis engine recognizes a "peak-trough-peak" waveform produced by aggregate particle events.

10. The fluidic system of claim 9, wherein the detection system includes a detector that receives photonic inputs from the interrogation zone and has a wide dynamic range defined as greater than or equal to 100 dB.

11. A method for drawing sample fluid from a sample container into an interrogation zone of a flow cytometer, comprising:

simultaneously pumping sheath fluid at a sheath flow rate from a sheath container through a flow cell, fluidicially coupled to the sample container, into the interrogation zone of the flow cytometer and pumping waste fluid at a waste flow rate from the interrogation zone into a waste container, wherein the sheath flow rate is different from the waste flow rate, thereby creating a pressure differential, and wherein the pressure differential draws the sample fluid from the sample container, through the flow cell with the sheath fluid into the interrogation zone at a sample flow rate;

collecting a data set of input signals from the sample fluid;

recognizing aggregate particle events in the data set with use of an algorithm; and automatically adjusting the sample flow rate based on the recognition of aggregate particle events in the data set, wherein adjusting the sample flow rate includes controlling at least one of the sheath flow rate and waste flow rate to adjust the pressure differential.

12. The method of claim 11, wherein adjusting the sample flow rate further includes adjusting a core stream diameter of the sample fluid.

13. The method of claim 12, wherein adjusting the core stream diameter of the sample fluid includes decreasing the core stream diameter after recognizing an aggregate particle event in the data set.

14. The method of claim 13, wherein decreasing the core stream diameter includes decreasing the core stream diameter to a diameter that forces particles in the sample fluid to flow in single file into the interrogation zone.

15. The method of claim 13, further comprising recognizing non-aggregate particle events in the data set, wherein adjusting the core stream diameter of the sample fluid further includes increasing the core stream diameter after recognizing a non-aggregate particle event in the data set.

16. The method of claim 15, further comprising repeating the step of adjusting the sample flow rate after at least one of (a) recognizing aggregate particle events and (b) recognizing non-aggregate particle events.

17. The method of claim 15, wherein adjusting the sample flow rate includes adjusting the sample flow rate after a predetermined ratio of aggregate particle events to non-aggregate particle events is recognized.

18. The method of claim 12, wherein adjusting the core stream diameter of the sample fluid includes increasing the core stream diameter in response to recognition of an aggregate particle event in the data set.

19. The method of claim 12, wherein adjusting the flow rate of the sample fluid includes adjusting the flow rate of the sample fluid after a predetermined number of aggregate particle events is recognized.

20. The method of claim 12, wherein collecting a data set of input signals from the sample fluid includes detecting a wide dynamic range of inputs greater than or equal to 100 dB.

* * * * *